US012811023B2

(12) United States Patent
Schmidt

(10) Patent No.: US 12,811,023 B2
(45) Date of Patent: Nov. 24, 2026

(54) DIRECT-ACTING VERTICAL LAMELLAE DRIVE

(71) Applicant: Varian Medical Systems, Inc., Palo Alto, CA (US)

(72) Inventor: Rolf Schmidt, Immenreuth (DE)

(73) Assignee: VARIAN MEDICAL SYSTEMS INC., Palo Alto, CA (US)

( * ) Notice: Subject to any disclaimer, the term of this patent is extended or adjusted under 35 U.S.C. 154(b) by 176 days.

(21) Appl. No.: 18/944,539

(22) Filed: Nov. 12, 2024

(65) Prior Publication Data

US 2026/0135011 A1 May 14, 2026

(51) Int. Cl.
*G21K 1/04* (2006.01)
*A61N 5/10* (2006.01)

(52) U.S. Cl.
CPC ........... *G21K 1/046* (2013.01); *A61N 5/1045* (2013.01)

(58) Field of Classification Search
CPC .............................. G21K 1/046; A61N 5/1045
See application file for complete search history.

(56) References Cited

U.S. PATENT DOCUMENTS 4,431,934 A * 2/1984 Kleinschmidt ...... H10N 30/206 310/331

* cited by examiner

*Primary Examiner* — Hugh Maupin
(74) *Attorney, Agent, or Firm* — Harness, Dickey & Pierce, P.L.C.

(57) ABSTRACT

A lamellae drive system includes a lamella moveably coupled to a carrier. The lamella includes a length extending parallel to a direction of motion of the lamella, and one or more groups of oscillating projections along at least a portion of the length of the lamella. A direction of oscillation of the oscillating projections is parallel to the direction of motion of the lamella, and the oscillating projections include opposing sloped surfaces oriented perpendicular to the direction of oscillation. The lamellae drive system includes two or more actuators. Each of the two or more actuators has an extendable dimension. The actuators are configured to drive the lamella by applying force to particular sloped surfaces of the one or more oscillating projections, with the force of the two or more actuators being applied out of phase with each other.

20 Claims, 8 Drawing Sheets

DIRECT-ACTING VERTICAL LAMELLAE DRIVE

TECHNICAL FIELD

This application relates generally to moving lamellae, and more specifically to moving lamellae using a direct-acting vertical drive.

BACKGROUND

The exact positioning of lamellae within medical devices is a challenge due to the accuracy, precision, safety, and reliability requirements. Satisfying these requirements may require guarding against external influences, which may occur in amplified form in devices used in conjunction with the application of radiation. In various medical devices, for example in multi-leaf collimators, the lamellae may conventionally be positioned by means of rotating motors, which act on the lamellae using gears, racks, spindle or the like. This usually requires additional sensor technology, since with the exception of stepper motors, it is not possible to determine the position of the lamellae to the necessary degree of accuracy. And even stepper motors may not achieve the necessary reliability.

SUMMARY

The scope of protection sought for various example embodiments is set out by the independent claims. The example embodiments and/or features, if any, described in this specification that do not fall under the scope of the independent claims are to be interpreted as examples useful for understanding various embodiments.

As described in more detail subsequently herein, a lamellae drive system employs actuators in conjunction with oscillating projections on the lamellae to move the lamellae. Some example embodiments may also measure position/movement of the lamellae based on a current actuator extension and/or a number of actuator extension cycles, without requiring additional sensors. The actuators may be positioned "vertically" with respect to the lamella, so that extension of the actuator applies force to the oscillating projections, causing the lamella to slide in a direction parallel to the oscillating projections.

As used herein, the term "vertical" should not be interpreted as being limited to being gravitationally vertical. To be sure, in example embodiments where lamellae are positioned side by side, with the lamellae tops pointing upward and lamellae bottoms pointing downward with respect to a gravitational frame of reference, actuators configured to contact the top (or bottom) of the lamellae may be positioned vertically with respect to the gravitational frame of reference. However, in various example embodiments, the orientation of the lamellae may be rotated before, during, or after use so that the "tops" and "bottoms" of adjacent lamellae may be positioned horizontally with respect to gravity, and thus may be considered to be "sides." An actuator positioned perpendicular to a length of one or more portions of a lamellae including oscillating projections may be said to be "vertical," even if the lamellae are horizontal, or at some other angle, with respect to a gravitational frame of reference.

In some example embodiments, the actuators may, but need not, be piezo stack actuators. The use of piezo stack actuators in some example embodiments may provide accurate, finely granular movement that does not require external sensors to determine lamellae movement or position. For example, an amount by which a piezo stick actuator is extended can be determined based on a voltage applied to the actuator, because a given voltage causes the actuator to extend by a given amount. Knowing the voltage applied means that the amount by which the actuator is extended is known, and the position of the lamellae may be determined.

In one or more example embodiments, a lamellae drive system includes a lamella moveably coupled to a carrier, the lamella including a length extending parallel to a direction of motion of the lamella; one or more groups of oscillating projections along at least a portion of the length of the lamella, a direction of oscillation of the oscillating projections being parallel to the direction of motion of the lamella, and the oscillating projections including opposing sloped surfaces oriented perpendicular to the direction of oscillation; and two or more actuators, each of the two or more actuators having an extendable dimension and being configured to drive the lamella by applying force to particular sloped surfaces of the one or more oscillating projections, the force of the two or more actuators being applied out of phase with each other. At least one of the one or more groups of oscillating projections may be integral to or affixed to the lamella.

In some such example embodiments, the one or more groups of oscillating projections may include at least a first group of oscillating projections aligned along a first axis of the lamella, and/or a plurality of groups of oscillating projections aligned in an out of phase relationship along separate parallel axes. The two or more actuators may include a first actuator configured to drive the lamella in a first direction by applying force to a first sloped surface of the first group of oscillating projections at a first time; and a second actuator configured to drive the lamella in the first direction by applying force to a second sloped surface of the first group of oscillating projections at a second time.

In some example embodiments, the two or more actuators may include a first actuator configured to position the lamella within a threshold distance of a target position; and a second actuator configured to provide fine adjustments to the position of the lamella within the threshold distance of the target position.

In some example embodiments, a lamellae drive system further includes processing circuitry configured to determine a position of the lamella based on a number of extension cycles associated with the two or more actuators and a current extension amount of the two or more actuators. In some such example embodiments the processing circuitry is further configured to control a direction of movement of the lamella by extending the two or more actuators during times the two or more actuators are located over particular sloped surfaces having heights that increase in a selected direction of movement. Additionally, at least one of the two or more actuators may include a piezo stack, and the processing circuitry may be configured to determine a current extension amount of the piezo stack based on a control voltage applied to the piezo stack.

In some example embodiments, a controller for a lamellae drive system comprises: memory storing a program of instructions; and a processor coupled to the memory, the processor configured to execute the program of instructions to cause the controller to control the lamellae drive system to drive a lamella in a direction of motion by extending two or more actuators out of phase with each other, the two or more actuators configured to apply force to one or more sloped surfaces of one or more groups of oscillating projections extending along at least a portion of a length of the lamella parallel to the direction of motion, and determine a current position of the lamella based, at least in part, on positions of the two or more actuators in relation to the one or more groups of oscillating projections.

In some example embodiments, the controller may be further configured to execute the program of instructions to cause the controller to determine a current position of the lamella based on a number of extension cycles of the two or more actuators and a current extension of the two or more actuators. In some such example embodiments, the processor is further configured to execute the program of instructions to cause the controller to determine the current extension of the two or more actuators based on a voltage applied to the two or more actuators.

In one or more example embodiments, the processor is further configured to execute the program of instructions to cause the controller to control a direction of movement of the lamella by extending the two or more actuators during times the two or more actuators are located over selected sloped surfaces having heights that increase in the direction of movement of the lamella.

In some example embodiments, the processor is further configured to execute the program of instructions to cause the controller to control a first actuator to drive the lamella in a first direction by applying force to a first sloped surface of a first group of oscillating projections at a first time; and control a second actuator to drive the lamella in the first direction by applying force to a second sloped surface of a second group of oscillating projections at a second time.

In any of the above example embodiments, the processor may be further configured to execute the program of instructions to cause the controller to control a first motive device to position the lamella within a threshold distance of a target position; and control the two or more actuators to provide fine adjustments to the position of the lamella within the threshold distance of the target position.

In one or more example embodiments, a method comprises driving a lamella in a direction of motion by extending two or more actuators out of phase with each other, the two or more actuators configured to apply force to particular sloped surfaces of one or more groups of oscillating projections extending along at least a portion of a length of the lamella, a direction of oscillation of the oscillating projections being parallel to a direction of motion of the lamella; and determining a current position of the lamella based, at least in part, on positions of the two or more actuators in relation to the one or more groups of oscillating projections.

Various example embodiments of a method include determining a current position of the lamella based on a number of extension cycles of the two or more actuators and a current extension of the two or more actuators; controlling a direction of movement of the lamella by extending the two or more actuators during times the two or more actuators are located over selected sloped surfaces having heights that increase in the direction of movement of the lamella; and/or controlling a first motive device to position the lamella within a threshold distance of a target position and controlling the two or more actuators to provide fine adjustments to the position of the lamella within the threshold distance of the target position.

Any or all of the above example embodiments, and other example embodiments disclosed herein, may be used in various combinations.

BRIEF DESCRIPTION OF THE DRAWINGS

Example embodiments will become more fully understood from the detailed description given herein below and the accompanying drawings, wherein like elements are represented by like reference numerals. The example embodiments are given by way of illustration only, and thus are not limiting of this disclosure.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. The use of similar or identical reference numbers in the various drawings is intended to indicate the presence of a similar or identical element or feature.

DETAILED DESCRIPTION

Various example embodiments will now be described more fully with reference to the accompanying drawings in which some example embodiments are shown.

Detailed illustrative embodiments are disclosed herein. However, specific structural and functional details disclosed herein are merely representative for purposes of describing example embodiments. It should be understood that there is no intent to limit example embodiments to the particular forms disclosed. On the contrary, example embodiments are to cover all modifications, equivalents, and alternatives falling within the scope of this disclosure. One or more example embodiments described herein may be combined.

Figure 1:
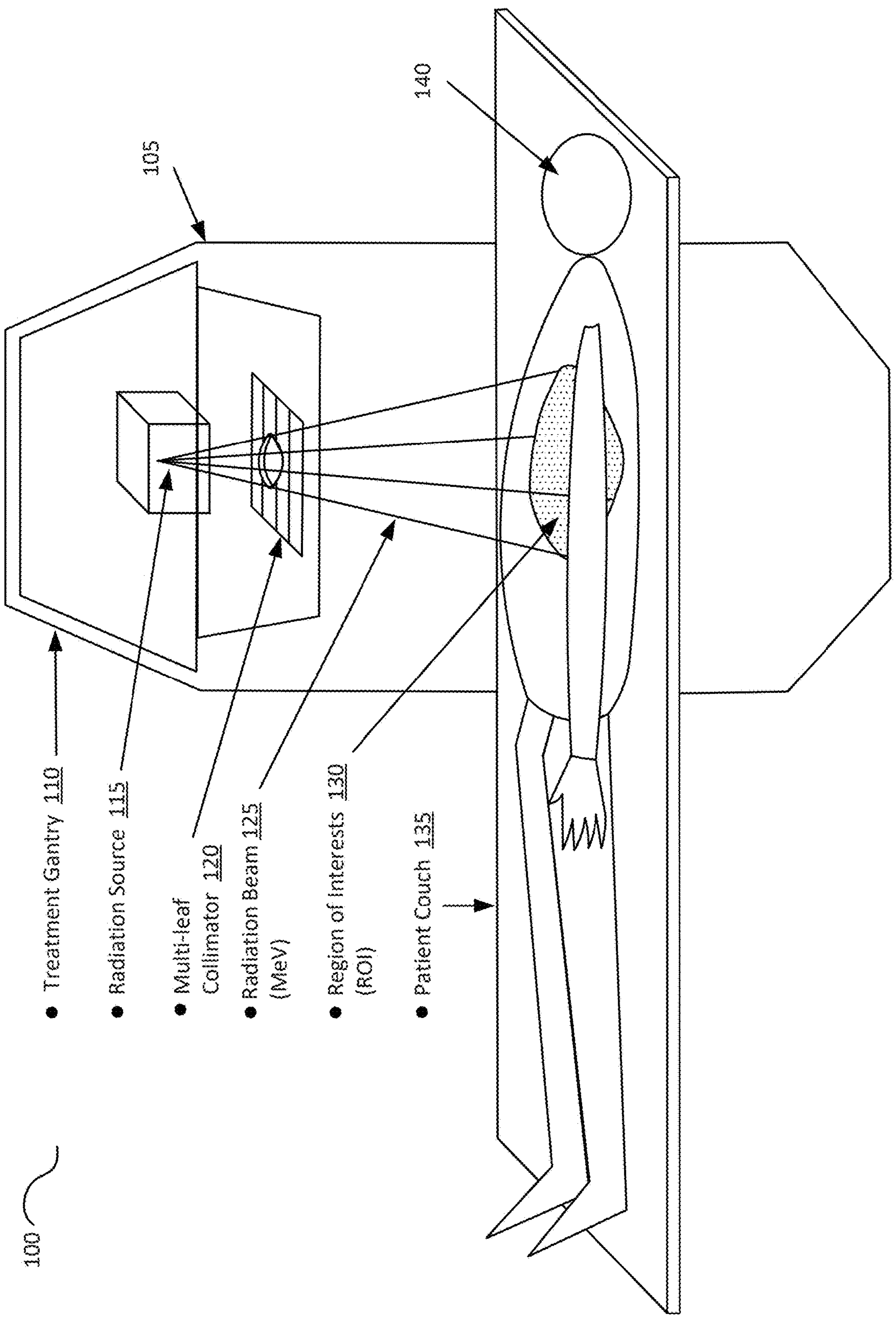
FIG. 1 is a pictorial representation of a system for providing medical treatment, in accordance with some example embodiments.

Referring first to FIG. 1, a system 100 for providing medical treatment will be discussed in accordance with various example embodiments. In the illustrated example embodiments, system 100 includes a patient couch 135, on which a patient 140 is positioned so that the region of interest 130 is properly located within the radiation beam 125. The treatment gantry 110 includes a radiation source 115 and a multi-leaf collimator 120. The radiation source 115 directs the radiation beam 125, through the multi-leaf collimator 120, and towards the region of interest 130. Individual lamellae of the multi-leaf collimator 120 are arranged to block portions of the radiation beam 125 that fall outside the region of interest 130.

In some example embodiments, the patient couch 135 includes multiple movable parts (not illustrated) used to position the patient couch 135 under the treatment gantry 110 and next to, within, or partially within the treatment unit 105. Furthermore, in some example embodiments the treatment gantry 110 may include movable parts that allow the treatment gantry 110 to be rotated about the patient couch 135 or otherwise moved relative to the region of interest 130. Movement of the treatment gantry 110 or the patient couch 135 may cause the region of interest 130 to move with respect to the radiation source 115 and the multi-leaf collimator 120. Changes in the relative position of the region of interest 130 may cause the shape and size of the region of interest to vary, which require individual lamellae of the multi-leaf collimator 120 to be moved to block different portions of the radiation beam 125.

Direct-acting vertical drive systems and techniques may be used to control and/or movements of movable parts included in the treatment gantry 110, the treatment unit 105, the patient couch 135, and/or the multi-leaf collimator 120.

Figure 2:
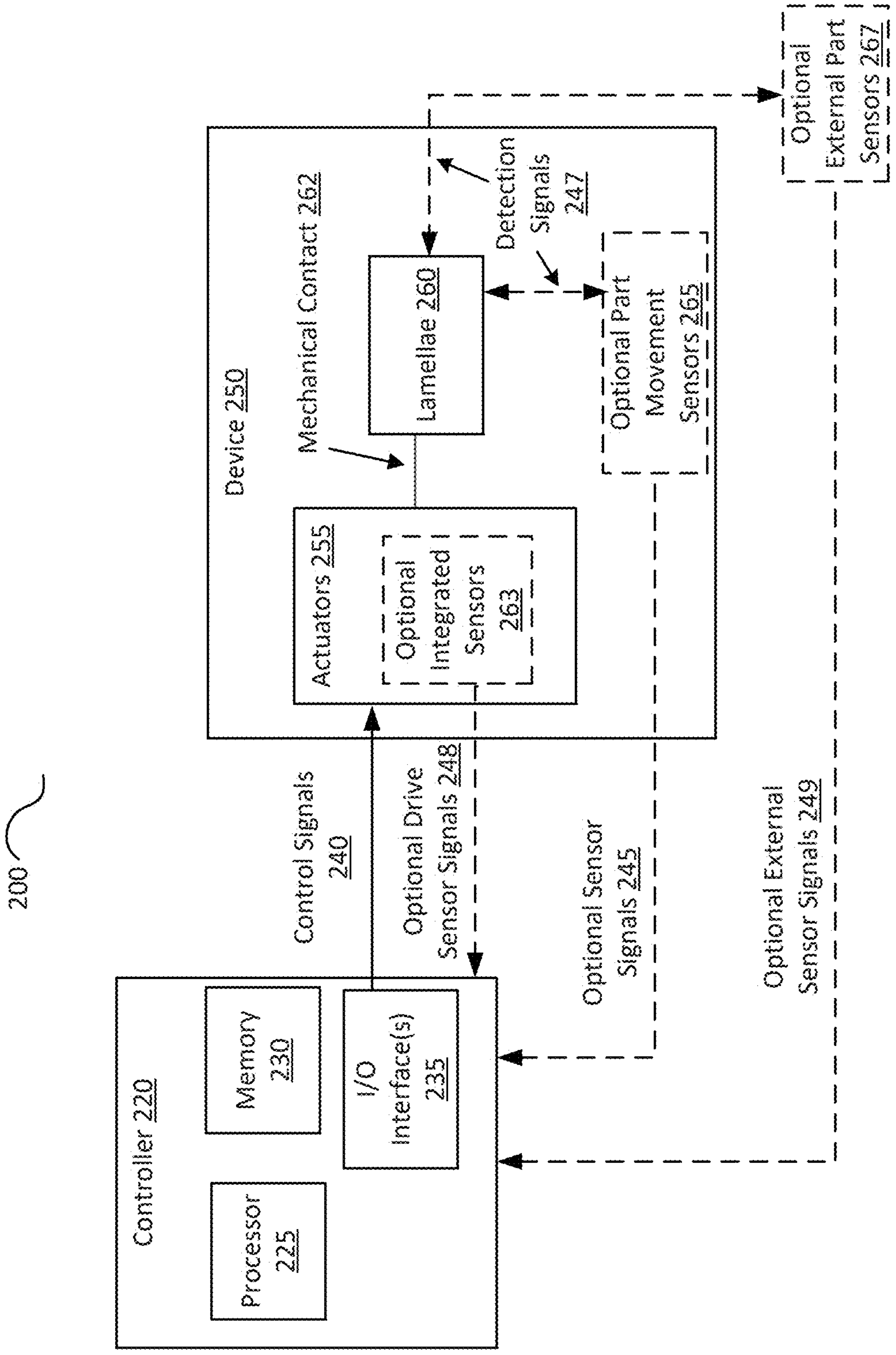
FIG. 2 is a block diagram of a lamellae drive system, in accordance with some example embodiments.

Referring next to FIG. 2, a lamellae drive system 200 will be discussed in accordance with various example embodiments. In the illustrated example embodiments, the lamellae drive system 200 includes device 250 and controller 220. Device 250 includes actuators 255. The actuators 255 may be direct-acting vertical devices physically coupled to lamellae 260 by direct mechanical contact 262, and are used in various example embodiments to impart motion to the lamellae 260 in conjunction with one or more groups of oscillating projections included on a lamella 260. The actuators 255 may include any of various types of linear actuators, including but not limited to, mechanical actuators, coiled actuators, lead screw actuators, telescoping actuators, hydraulic actuators, or piezoelectric actuators, which are sometimes referred to herein as piezo stacks.

The actuators 255 may, but need not, include optional integrated sensors 263. Device 250 may also include optional part movement sensors 265 in place of, or in addition to, the optional integrated sensors 263. It should be noted that in at least one example embodiment, for example where the actuators 255 are piezo stacks, the amount of extension of the of the piezo stack need not be measured. Instead, the amount of extension of the actuators 255 may be determined from a control voltage applied to the actuators 255, which can be used in conjunction with known characteristics of oscillating projections on the lamellae 260 to determine a position and movement of the lamellae 260, without requiring any motion or position sensors. Controller 220 includes a processor 225, memory 230, and input/output (I/O) interfaces 235.

In one or more example embodiments, the actuators 255 impart motion to the lamellae 260 along one or more axes by pressing against sloped portions of oscillating projections formed on or affixed to the lamellae 260. In some such example embodiments, a first actuator may apply downward force to a first sloped portion of an oscillating projection having a first orientation, so that the lamellae is pushed in a desired direction, while a second actuator is in contact, but not applying downward force, to an oppositely oriented sloped portion of the same or a different oscillating projections. This mechanism of movement will be discussed subsequently in greater detail. In at least one example embodiment, a set or group of the lamellae 260 are moved along parallel axes by different sets of actuators 255, although at least some example embodiments are not limited to lamellae movement along parallel axes.

The optional integrated sensors 263 may be used to sense a force being applied by actuators 255, an amount of extension associated with individual actuators, count a number of extensions, or the like. Various types of optional integrated sensors may include, but are not limited to, contact and/or contactless sensors that obtain movement and/or position information from which a position of one or more of the lamellae 260 may be inferred. The optional integrated sensors 263 may include, but are not limited to, strain gauges, magneto-strictive drive-spindle sensors, glass scales, capacitive measurement systems, optical encoders or other visual systems, or the like. The term "sensor" may be used herein to refer to an individual sensing element, or to a collection/group of sensing elements that cooperate to perform a sensing function.

The optional part movement sensors 265 may include sensors of the same or different types as optional integrated sensors, and may be used to sense and/or measure position or movement of single or multiple lamellae in example embodiments employing the optional part movement sensors 265.

In operation, the processor 225 included in the controller 220 generates control signals 240, and transmits those control signals to the actuators 255 of device 250. In at least one example embodiment, the control signals 240 include voltage control signals applied to piezo-stack actuators included in actuators 255. The voltage control signals may be timed so that actuators 255 used to drive a particular lamella are extended and/or retracted in an out of phase relationship with each other, as discussed subsequently in greater detail. The actuators 255 may be extended out of phase with each other in response to the voltage control signals, causing the actuators 255 to apply force to the oscillating projections on the lamellae 260. The sloped nature of the oscillating projections translates the direction of the downward force applied by the actuators 255, thereby imparting motion to the lamellae.

In some example embodiments, a voltage control signal applied to an actuator being retracted may be controlled to ensure that the retracting actuator remains in contact with a surface of the oscillating projections. In one or more example embodiments, by applying known control signals both to actuators being extended and retracted, the actuators may be used to "lock" the actuator at its current location, thereby reducing the potential for accidental movement of the lamella.

Changes in position of the lamellae 260 may be determined by the controller based on current voltage control signals being applied to the actuators 255, a history of the control signals 240 transmitted to the actuators 255, and/or characteristics of the oscillating projections. Assume, for example, that each oscillating projection has a "wavelength" of 1 mm, and an "amplitude" of 0.5 mm. In some such example embodiments, a single, 0.5 mm extension of an actuator perpendicular to the lamella, will move the lamella 0.5 mm. If the voltage applied to the actuator is sufficient to extend the actuator a distance of only 0.25 mm (e.g. half an extension) then the lamella will move a distance of 0.25 mm. Thus, if the controller fully extends the actuator four times, and the actuator is currently half-extended (e.g., 4.5 extension cycles) the lamella will have been moved 2.25 mm from its previous position. The controller may alter the direction of lamellae movement by applying a control voltage to an actuator that is currently over an oppositely oriented slope of the oscillating projection.

In some example embodiments, the controller 220 may receive, for example at I/O interfaces 235, optional drive sensor signals 248 generated by optional integrated sensors 263, optional sensor signals 245 generated by the optional part movement sensors 265 and/or optional external sensor signals 249 generated by optional external part sensors 267.

In various example embodiments, the optional part movement sensors 265 and/or optional external part sensors 267 are contactless sensors that generate and sense detection signals 247, which may be considered "contactless" signals. As used herein, the term "contactless," "contactless sensing," and similar terms refer to interactions between an object and an electrical signal an electromagnetic signal, such as light, magnetic field(s), soundwaves detectable or undetectable by the human hear, or the like, but without physical contact between two objects.

Figure 3:
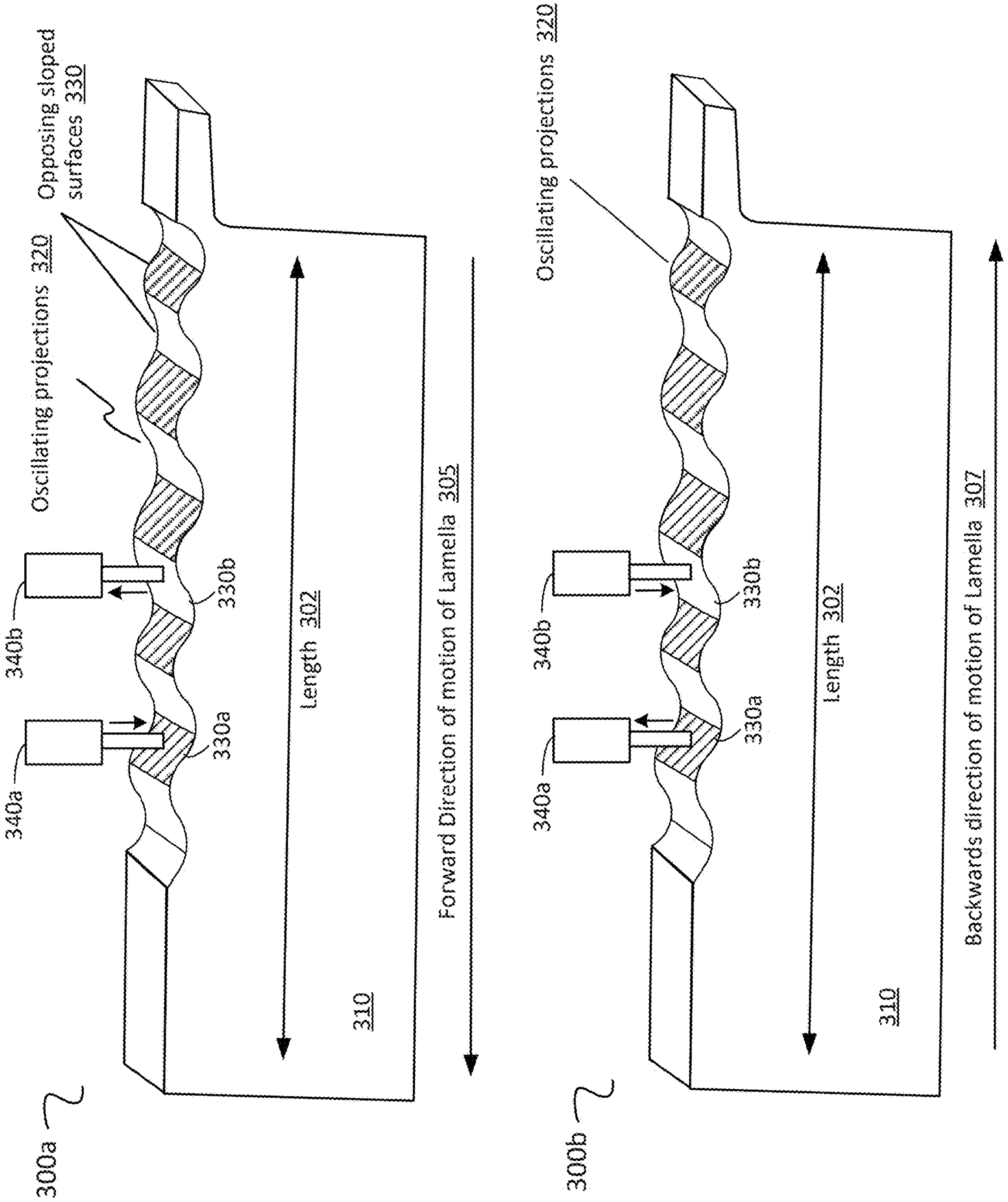
FIG. 3 is a diagram illustrating movement of lamellae using a direct-acting vertical drive, in accordance with some example embodiments.

Referring next to FIG. 3, moving lamellae using a direct-acting vertical drive will be discussed in accordance with some example embodiments. FIG. 3 includes a first diagram 300*a*, in which a lamella 310 is being moved in a forward direction 305, and a second diagram 300*b*, in which the lamella 310 is being moved in a backwards direction 307. The lamella 310 includes a group of oscillating projections 320 oscillating along a length 302 of the lamella 310. The oscillating projections 320 may be, in some example embodiments, molded, etched, cut, ground, or otherwise formed as part of lamella 310. In other example embodiments, the oscillating projections 320 may be attached, mounted, or otherwise affixed to lamella 310.

As illustrated in the example embodiment of FIG. 3, the group of oscillating projections 320 oscillate along an axis of motion of the lamella 310, with each oscillation including opposing sloped faces 330. In some example embodiments, the oscillating projections 320 do not oscillate along an axis of movement of the lamella 310, but may instead oscillate along an axis intersecting the angle of movement. The axis of oscillation may be in a vertical direction, a horizontal direction, or some combination thereof.

In various example embodiments, the opposing sloped faces 330 are themselves oriented perpendicular to the direction of oscillation. In some example embodiments, the opposing sloped faces 330 may not be exactly perpendicular, but instead are oriented at another angle to the direction of oscillation, such that a force applied to a sloped face imparts motion to the lamella 310 in a desired direction of motion.

In an example embodiment of operation, first actuator 340*a* may be extended to apply force to first opposing sloped faces 330, in response to which the lamella 310 moves in the forward direction 305. During the time that first actuator 340*a* is applying downward force to the first opposing sloped surface 330*a*, second actuator 340*b* may be actively controlled to retract or allowed to retract. Actively retracting second actuator 340*b* may include applying a retraction-control signal to the second actuator 340*b*. Allowing the second actuator 340*b* to retract may include simply not applying a control signal to the second actuator 340*b*, thereby allowing pressure applied to an extended portion of the second actuator 340*b* during movement of the second opposing sloped surface 330*b* to push the second actuator 340*b* closed.

At some point during movement of the lamella 310, the first actuator 340*a* will reach the bottom of the trough between the first opposing sloped surface 330*a* and the second opposing sloped surface 330*b*. In at least one example embodiment, the lowest point of the trough corresponds to full extension of the first actuator 340*a*. In at least one example embodiment, the first actuator 340*a* and the second actuator 340*b* are positioned so that at the same time the first actuator 340*a* is located over the trough, and fully extended, the second actuator 340*b* is positioned over a peak of the same or a different oscillating projection, and is fully retracted. As used herein, this relationship is referred to herein as being "out of phase." At the point where the first actuator 340*a* is fully extended, and the second actuator 340*b* is fully retracted, movement in the forward direction 305 may be maintained by extending the second actuator 340*b*, while the first actuator 340*a* is retracted or allowed to retract.

The above process may be reversed to drive the lamella 310 in the reverse direction 307, by using first actuator 340*a* and second actuator 340*b* to apply out of phase force to surfaces facing a same direction. That is the two actuators may press down on different, same-facing (non-opposing) surfaces of the oscillating projections at different times to impart motion to lamella 310.

In some example embodiments, different sets of actuators may be used for forward and reverse motions. In some such example embodiments, pins extending from the actuators may, but need not, be beveled in accordance with the desired direction of motion. In other example embodiments, sets of actuators may be tilted to facilitate movement in a particular direction, or a tilt of the actuator may be adjusted by control signals based on a desired direction of movement. In at least one example embodiment, however, a perpendicular force applied to the set of oscillating projections 320 by fixed-position actuators may be used to impart motion to lamella 310.

Figure 5:
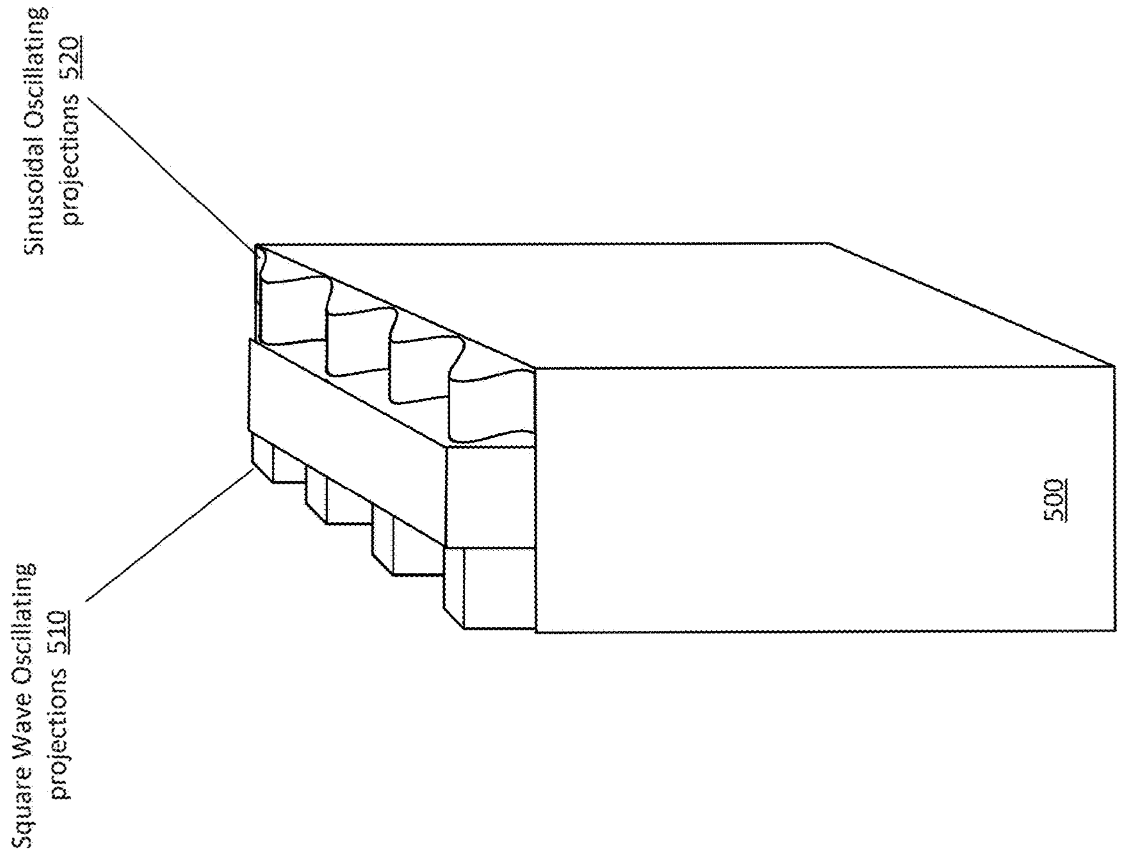
FIGS. 4 and 5 are diagrams illustrating various types of oscillating projections, in accordance with some example embodiments.
Figure 4:
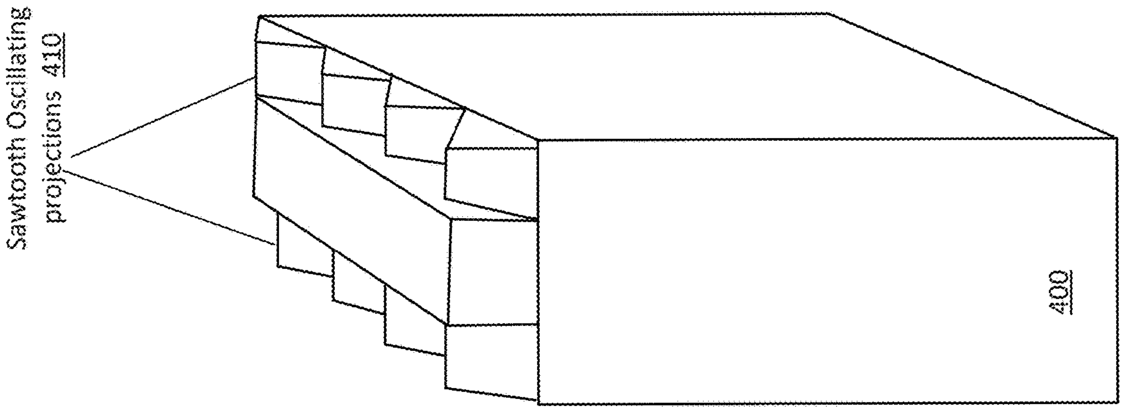

Referring next to FIGS. 4 and 5 various types of oscillating projections will be discussed in accordance with some example embodiments. FIG. 4 shows sawtooth oscillating projections 410 formed or affixed to lamella 400. The example embodiment of FIG. 4 includes two separate sets of sawtooth oscillating projections 410. In some example embodiments, two or more actuators may be located over each set of oscillating projections. The actuators may be positioned adjacent to each other, relying on an offset between the two sets of oscillating projections to provide an "out-of-phase" relationship used for movement in one or more example embodiments. Alternatively, the two sets of sawtooth oscillating projections may be substantially in phase with each other and the location of the actuators may be offset to provide an "out-of-phase" relationship. In some example embodiments, one set of oscillating projections may be used for movement in one direction, and a second set of oscillating projections may be used for movement in another direction. In some example embodiments, clipped sawtooth oscillating projections may be used, and/or the peaks and valleys of the sawtooth oscillating projections 410 may be rounded.

FIG. 5 illustrates a lamella 500 including multiple groups of oscillating projections having different shapes. In the illustrated example embodiment, lamella 500 includes a group of square-wave oscillating projections 510 and a group of sinusoidal oscillating projections 520. In at least one example embodiment, the walls of the square-wave oscillating projections 510 may be slightly sloped. However, in at least some example embodiments, a protruding portion of the actuators may be beveled, and/or the actuators may be positioned at an angle to provide a relative slope.

In some example embodiments, the periodicity and/or amplitude of the oscillating projections may vary between groups of oscillating projections, or within a single group of oscillating projections. The basic shape of the groups of oscillating projections may also vary between and within groups. In some example embodiments, more than two groups of oscillating projections may be used on a single or multiple axes. Furthermore, some example embodiments may include multiple groups of oscillating projections along each of multiple different axes.

Figure 6:
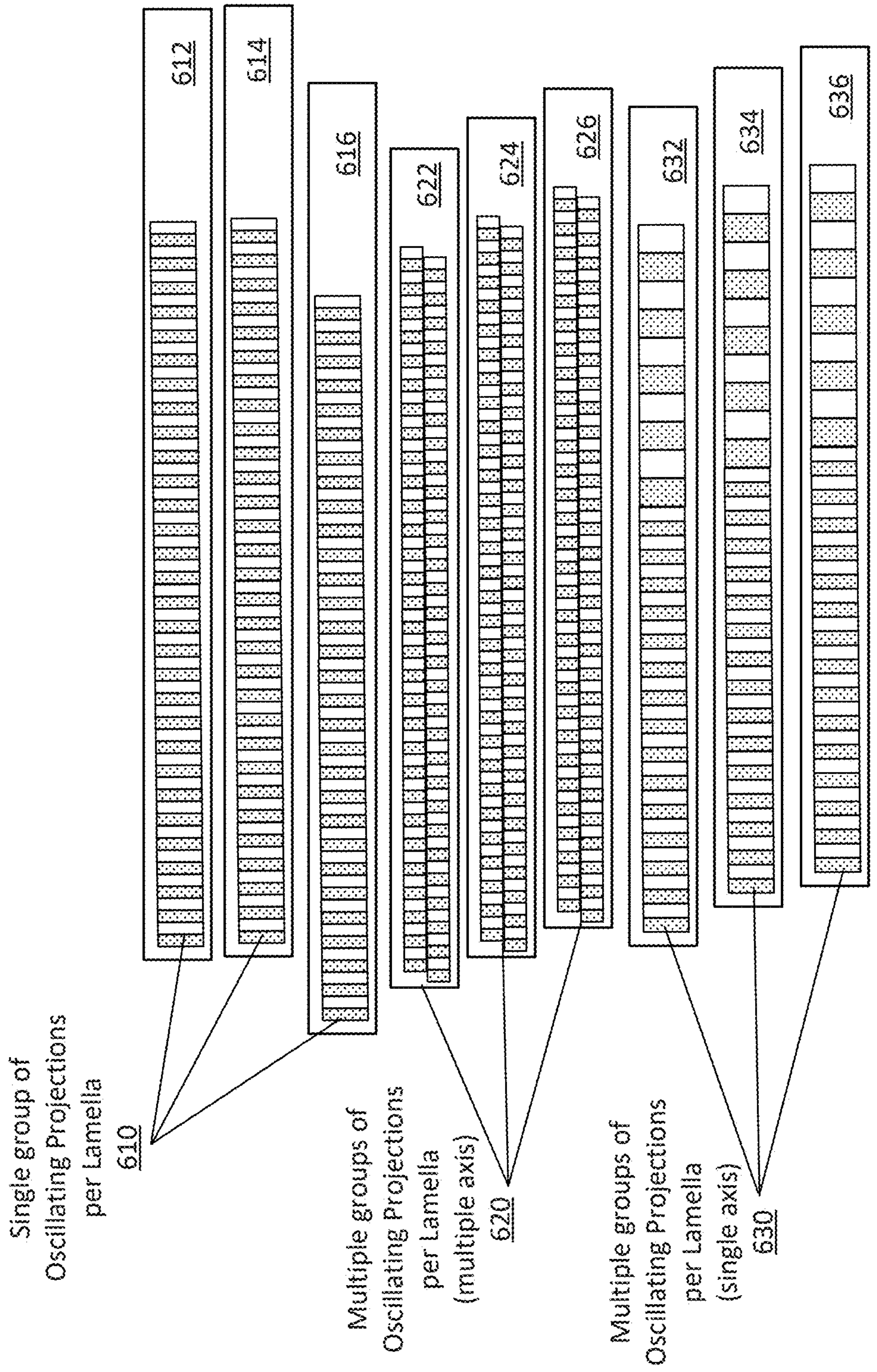
FIG. 6 is a diagram illustrating various arrangements of groups of oscillating projections, in accordance with some example embodiments.

Referring next to FIG. 6, lamellae including different arrangements of groups of oscillating projections will be discussed in accordance with some example embodiments. Three lamellae, 612, 614, and 616, each include single groups 610 of oscillating projections. A second three lamellae, 622, 624, and 626 each include multiple of multi-axis groups 620 oscillating projections. The final three lamellae, 632, 634, and 636 each include multiple groups of oscillating projections along a single axis 630.

Lamella 310 (FIG. 3) is an example embodiment of a single group 610 of oscillating projections per lamella. Lamella 400 (FIG. 4) and lamella 500 (FIG. 5) are examples of multi-axis groups 620 of oscillating projections. The multiple groups of oscillating projections along a single axis 630, as shown by lamellae, 622, 624, and 626, may each have varying shapes, periodicity, and or amplitudes. In some example embodiments, multiple groups lying along the single axis 630 may be implemented as a single group of oscillating projections with smoothly varying periodicity, and/or amplitudes.

In some example embodiments, the widths and/or lengths of a group or groups of oscillating projections may vary. Where multiple groups on different axes are employed, the widths may be different or the same. Furthermore, the width of oscillating projections may, but need not, vary even within a single group of oscillating projections. In other example embodiments, amplitudes, oscillating frequency (periodicity), widths, lengths, waveshapes, or some combination thereof may be equal or different within and/or between groups of oscillating projections.

Figure 7:
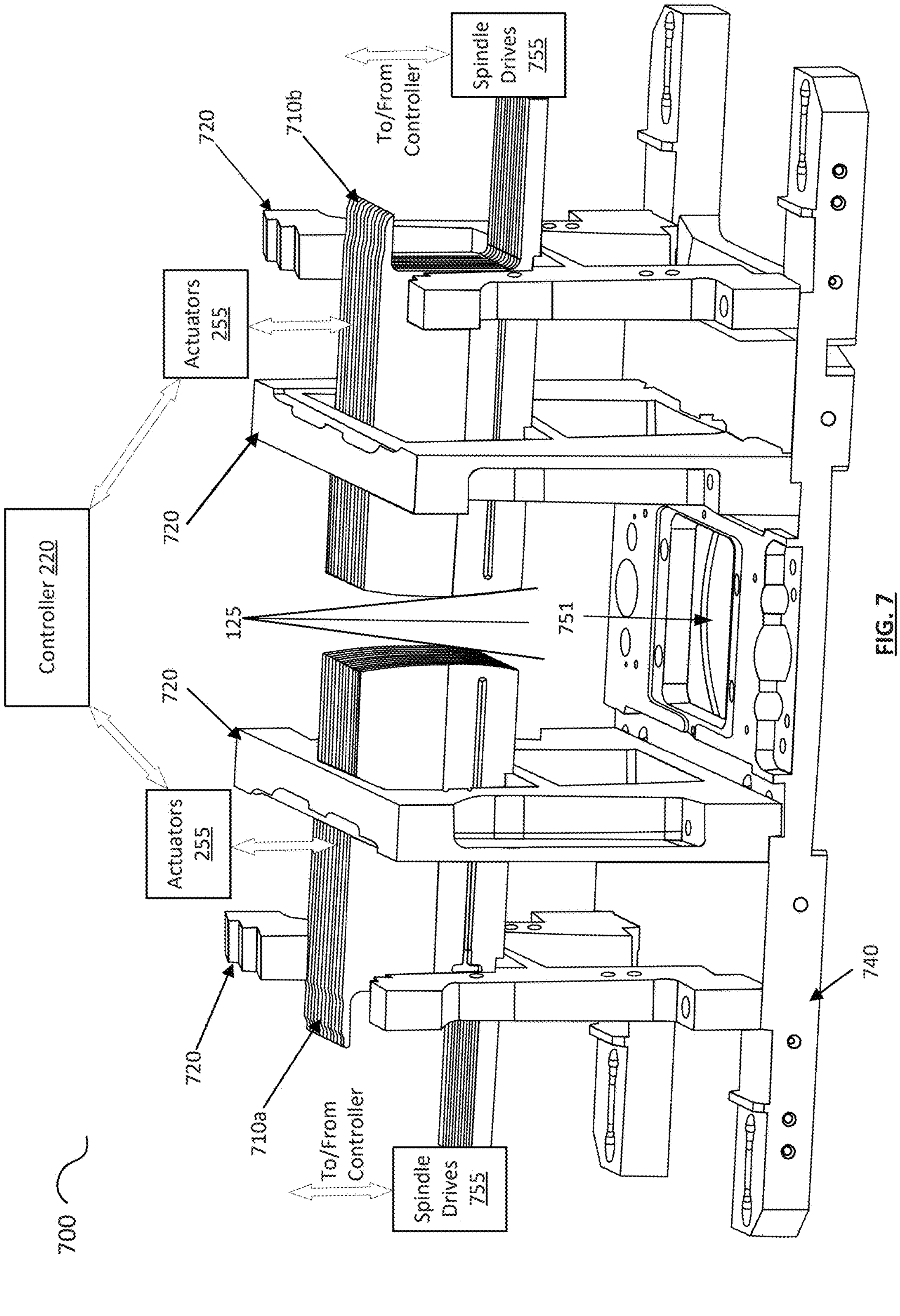
FIG. 7 is a diagram of a collimator box including collimator lamellae, in accordance with some example embodiments.

Referring next to FIG. 7, a diagram of a collimator box 700 including collimator lamellae will be discussed in accordance with various example embodiments. In the illustrated example embodiments, multiple collimator lamellae 710*a* and 710*b* within the collimator box 700 are movably supported by a leaf holders 720, which support the collimator lamellae 710*a* and 710*b*, and allow individual lamella to move independently from each other along parallel movement axes. The leaf holders 720 are mounted on base 740, which includes a target opening 751 in the center.

In an example of operation, a radiation beam 125 is directed between the collimator lamellae 710*a* and 710*b*. The radiation beam 125 is directed between the collimator lamellae and through target opening 751. The collimator lamellae 710*a* and 710*b* may be moved using actuators 255, under control of controller 220, to block portions of the radiation beam 125 during treatment of a patient. In some example embodiments, spindle drives 755 may be used to provide coarse positioning of the collimator lamellae 710*a* and 710*b*, while actuators 255 provide fine position adjustment. In other example embodiments, actuators 255 are used for both coarse and fine positioning. In some such example embodiments, coarse adjustment using actuators 255 may, but need not, include using lower-periodicity oscillating projections to coarsely position the lamellae, and high periodicity oscillating projections to provide fine positioning.

In some such example embodiments, optional sensors included in the spindle drive 755, or optional external sensors, may be used to determine the position of the collimator lamellae 710*a* and 710*b*. The optional sensors may transmit sensing signals indicating changes in position of collimator lamellae 710*a* and 710*b* to controller 220, which in turn transmits control signals to spindle drives 755 that move collimator lamellae in accordance with the control signals until a coarse target location is reached. The sensing and movement process may be iteratively repeated until each collimator leaf reaches the coarse target position.

In at least one example embodiment, positioning of the collimator lamellae 710*a* and 710*b* does not require any sensors; instead, positions of the collimator lamellae 710*a* and 710*b* may be determined based on the control signals provided to the actuators 255. Consider the following example of operation in which a single lamella is to be moved to a target position from a previous position. It is assumed for purposes of this example embodiment that the controller 220 is aware of the current position of the lamella, which may be located at a previous target position, or at a coarse target position. The controller 220 may be instructed, for example by user input, by a treatment program, or the like, to move one lamella to a target location located 4.25 mm forward.

The controller may determine, for example based on a known distance between peaks of a group of oscillating projections and a current extension of an actuator, that each extension of a single actuator will move the lamella 0.5 mm. The controller may determine to extend two out-of-phase actuators four times each, resulting in movement of the lamella by 4 mm, and then extend one of the actuators ½ way to achieve the 0.25 mm of movement, and place the lamella at the target location.

Figure 8:
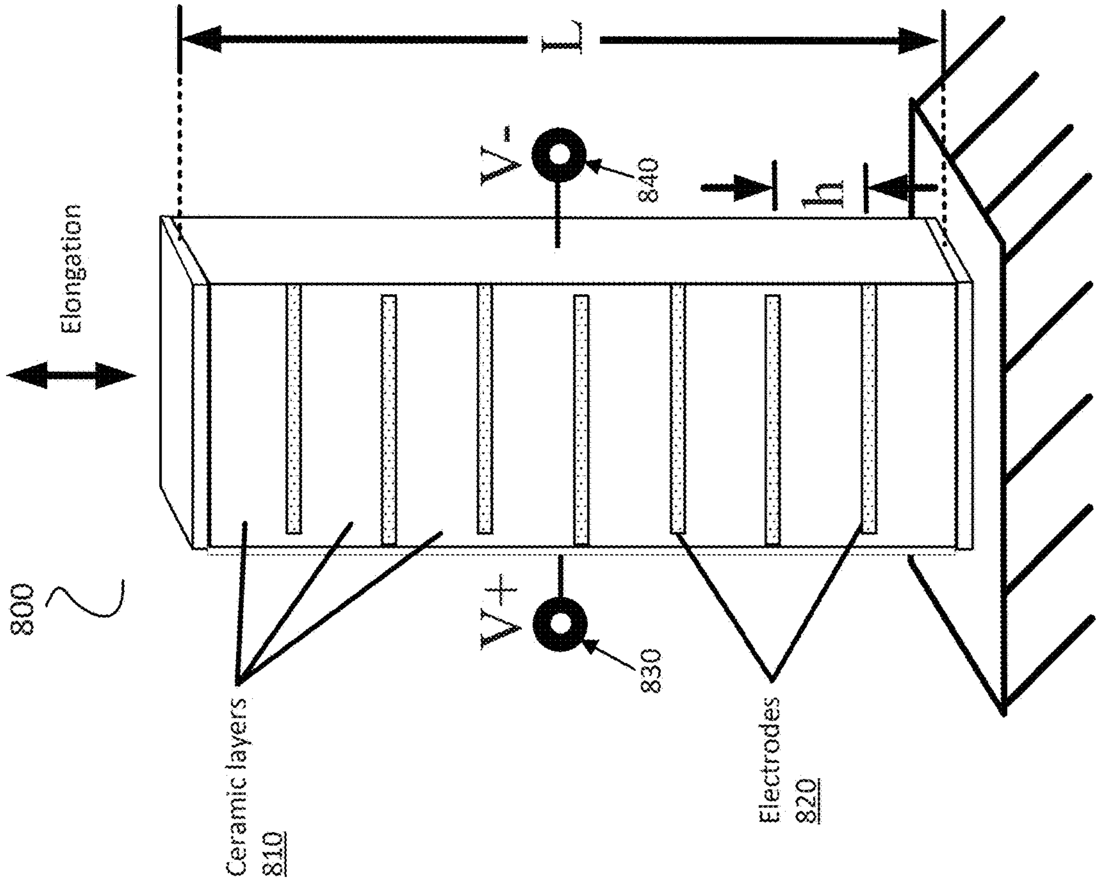
FIG. 8 is a diagram illustrating a piezo-electric stack, in accordance with some example embodiments.

Referring next to FIG. 8, a piezo-electric stack (piezo stack) 800 will be discussed in accordance with some example embodiments. Piezo stack 800 includes ceramic layers 810 with electrodes 820 interspersed between ceramic layers. Each of the electrodes 820 is electrically coupled to either a positive terminal 830 or a negative terminal 840. Without a control voltage applied between the positive terminal 830 and the negative terminal 840, each of the ceramic layers 810 has a height h, which are included in the overall length L of piezo stack 800. Applying a voltage to the piezo stack 800 causes the piezo stack to deform, for example by elongating in the direction indicated. In various example embodiments, each of the ceramic layers 810 of the piezo stack 800 deforms by an amount proportional to the strength of an electric field generated between the electrodes 820 adjacent to the ceramic layers 810. Because the strength of the electric field is dependent on the voltage applied between the positive terminal 830 and the negative terminal 840, the amount of deformation, e.g. the amount of extension, in the length L may be determined from control signals supplying the voltages to the positive terminal 830 and the negative terminal 840. The total elongation of piezo stack 800 may be between about 0.1 and 0.15 percent of the piezo stack. In some example embodiments, 100's of volts may be required to cause millimeters of length extension.

Figure 9:
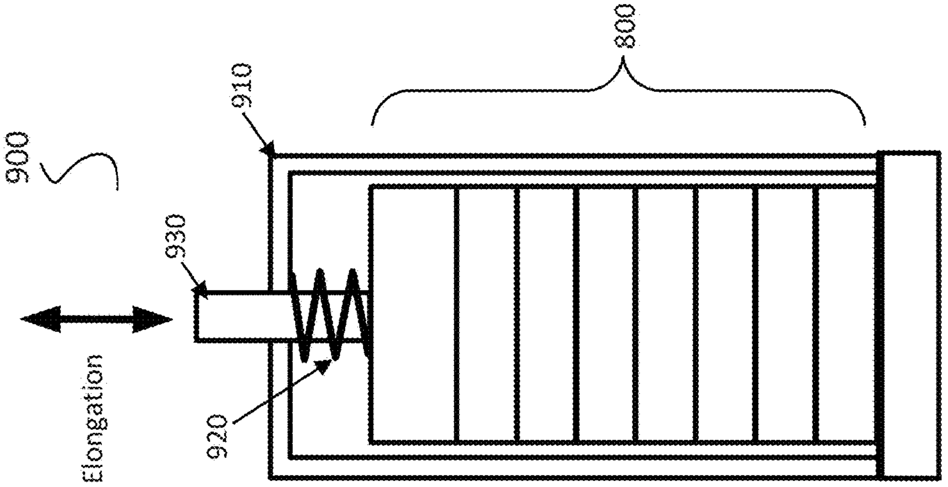
FIG. 9 is a diagram illustrating an actuator including a piezo-electric stack, in accordance with some example embodiments.

Referring next to FIG. 9, a piezoelectric actuator 900 including a piezo stack 800 will be discussed in accordance with some example embodiments. Piezoelectric actuator 900 may include a housing 910, which includes an opening through which a piston 930 may move in response to piezo stack 800 elongating when a control voltage is applied. In at least one example embodiment, the accuracy of the piezoelectric actuator 900 may be between about 0.01 mm to 0.1 mm. A spring 920 may be used to pre-load the piezoelectric actuator 900. In other example embodiments, preloading may be done outside of the housing 910. Preloading the piezoelectric actuator 900 to a value greater than an expected tensile load helps maintain the piezoelectric actuator 900 in compression to facilitate operation in highly dynamic, bi-directional applications.

Figure 10:
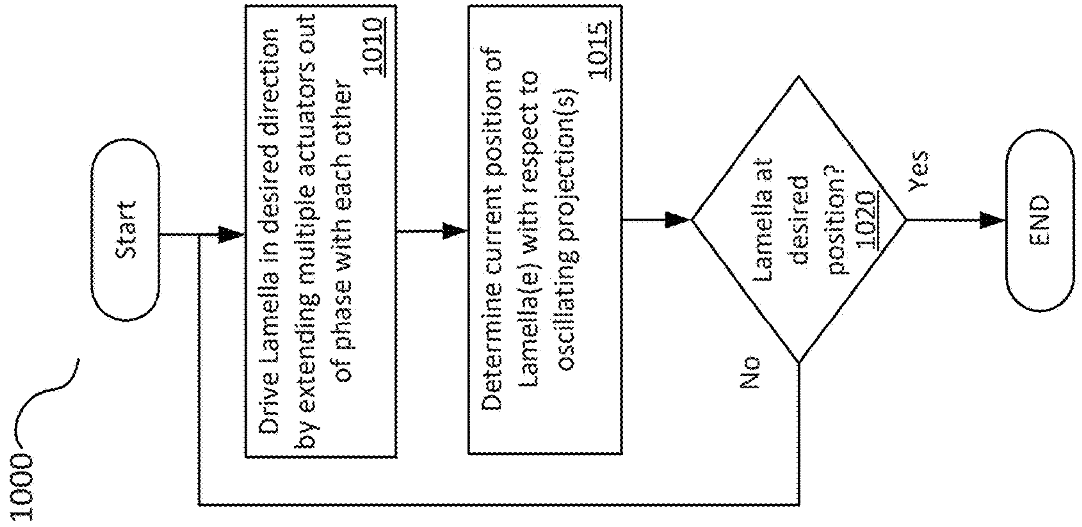
FIG. 10 is a flowchart illustrating a method of positioning lamellae, in accordance with some example embodiments.

Referring next to FIG. 10, a method 1000 of positioning lamellae will be discussed in accordance with some example embodiments. As illustrated by block 1010, the lamellae are driven in a desired direction by extending multiple actuators out of phase with each other. Extending the actuators out of phase with each other may be accomplished by extending and/or retracting multiple actuators to apply force to particular faces of oscillating projections that are part of each lamella. Actuators may be iteratively extended, retracted, and/or allowed to retract in a pattern that applies force to faces of the oscillating projections that are oriented in the same direction. Movement of the lamellae, as well as different oscillating projection configurations, have been previously discussed with reference to FIGS. 3-6.

As illustrated by block 1015, in at least one example embodiment a controller, for example, controller 220 (FIG. 2), determines the current position of the lamellae with respect to the oscillating projections. Because the oscillating projections have a fixed relationship to the lamellae, the absolute positions of the lamellae, the positions of the lamellae with respect to the carrier, or the positions of the lamellae with respect to other frames of reference may be determined.

In at least one example embodiment, the current positions of the lamellae may be determined by a controller counting the number of extension and/or retraction cycles of the actuators and converting the number of extension/retraction cycles to distances based on the characteristics of the oscillating projections associated with lamellae; determining current extension amounts of the actuators; converting the current extension amounts to distances based on the characteristics of the oscillating projections; obtaining starting locations of the lamellae from memory; and adding/subtracting the distances corresponding to the number of extension/retraction cycles and the distances associated with the current extension amounts of the actuators, to/from the starting locations.

As illustrated by block 1020, the controller may compare the current positions of the lamellae against target positions of the lamellae. The target positions of the lamellae may be determined by the controller by retrieving previously stored target positions from a memory, or based on real-time or near-real-time user input. In at least one example embodiment, the target positions of the lamellae may be stored in the memory and accessed by the controller as part of a given or predetermined sequence of events, such as a treatment plan that relates combinations of time, position of the patient, orientation of a treatment apparatus, and/or other similar inputs to particular lamellae target positions. In at least one example embodiment, if a current position of a lamella is within a threshold distance of a target position, the lamella is considered to be at the target position. In at least one example embodiment, the threshold may be +/−0.5% of a target position, but in other example embodiments, the threshold may be between about +/−0.1% to +/−10%. Different thresholds may be dependent on the different types of actuators used in a particular implementation.

Figure 11:
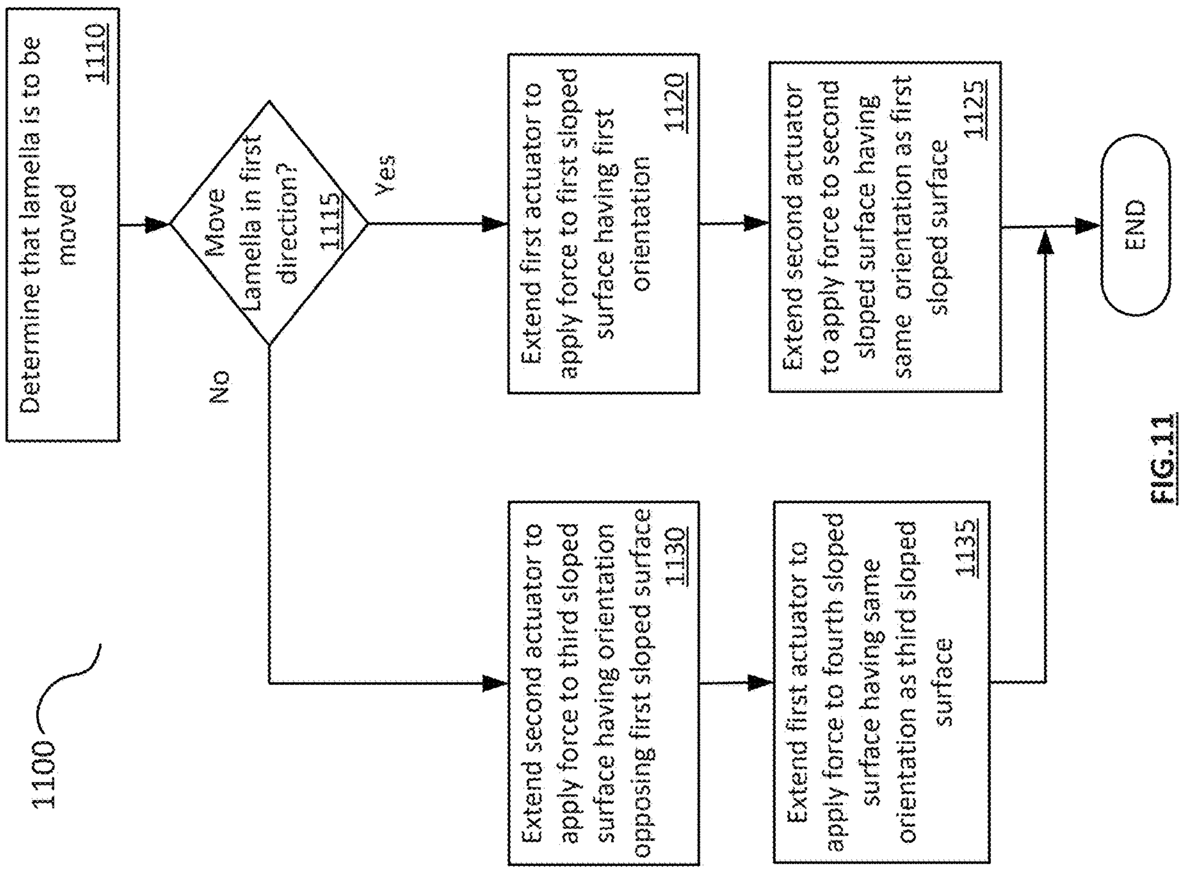
FIG. 11 is a flowchart illustrating a method of driving lamellae, in accordance with some example embodiments.

Referring next to FIG. 11, a method 1100 of driving lamellae will be discussed in accordance with some example embodiments. As illustrated by block 1110, a controller, for example, controller 220 (FIG. 2), determines that one or more lamellae are to be moved. This determination may be made in accordance with a previously stored treatment plan, and/or in response to stored or substantially real-time user input.

As illustrated by block 1115, the controller determines a direction in which the one or more lamellae are to be moved. In at least one example embodiment, a lamellae may be moved either forward or backwards along an axis of movement. In at least one example embodiment, the direction of movement may not be linear and may be, for example, clockwise and counterclockwise. However, in the illustrated example embodiments, the first direction may be considered to be a linear (as opposed to rotational) forward direction, and the second direction may be considered to be a linear reverse direction. The direction in which the one or more lamellae are to be moved may be determined based on a relationship between a current position of the lamellae and a target position of the lamellae, where the target location may be specified by a treatment plan or user input.

As illustrated by block 1120, if the determination at block 1115 indicates that a lamella is to be moved in a first direction, the controller applies a first control signal to a first actuator, thereby causing the first actuator to extend and apply force to a first sloped surface of a group of oscillating projections associated with the lamella to be moved in the first direction. By applying force to the first sloped surface, which has a first orientation with respect to the lamella, the first actuator drives the lamella in the first direction. In some example embodiments, at the same time the first actuator is being extended, a second actuator may be retracted so that that the second actuator remains in contact with another sloped surface of the same group of oscillating projections, or with a sloped surface of a different group of oscillating projections.

As illustrated by block 1125, the controller applies a second control signal to a second actuator, thereby causing the second actuator to extend and apply force to a second sloped surface of a group of oscillating projections associated with the lamella to be moved in the first direction. By applying force to the second sloped surface, which has the same orientation with respect to the lamella as the first sloped surface, the second actuator drives the lamella further along in the first direction. In at least one example embodiment, at the same time the second actuator is being extended the first actuator may be retracted, so that that the first actuator remains in contact with the first sloped surface while the lamella is being driven by the second actuator. It will be noted that extending the first actuator while retracting the second results in the first and second actuator being extended out of phase with each other.

As illustrated by block 1130, if the determination at block 1115 indicates that a lamella is not to be moved in the first direction, movement in the second, or opposite, direction is indicated. When movement in the second direction is indicated, the controller applies a third control signal to the second actuator, thereby causing the second actuator to extend and apply force to a third sloped surface having an orientation opposing the orientation of the first sloped surface. Applying force to the third sloped surface causes the lamella to move in the second direction. As with movement in the first direction, at the same time the second actuator is being extended, the first actuator may be retracted so that it remains in contact with another sloped surface of the same group of oscillating projections or with a sloped surface of a different group of oscillating projections.

As illustrated by block 1135, the controller applies a fourth control signal to the first actuator, thereby causing the first actuator to extend and apply force to a fourth sloped surface having an orientation opposing the orientation of the first sloped surface, and matching the orientation of the third sloped surface. Applying force to the fourth sloped surface causes the lamella to move further in the second direction. During a time the first actuator is being extended, the second actuator may be retracted so that it remains in contact with the third sloped surface.

Various non-limiting illustrative embodiments are disclosed herein.

In illustrative embodiment 1, a lamellae drive system comprises a lamella moveably coupled to a carrier, the lamella including a length extending parallel to a direction of motion of the lamella; one or more groups of oscillating projections along at least a portion of the length of the lamella, a direction of oscillation of the oscillating projections being parallel to the direction of motion of the lamella, and the oscillating projections including opposing sloped surfaces oriented perpendicular to the direction of oscillation; and two or more actuators, each of the two or more actuators having an extendable dimension and being configured to drive the lamella by applying force to particular sloped surfaces of the one or more oscillating projections, the force of the two or more actuators being applied out of phase with each other.

In illustrative embodiment 2, the one or more groups of oscillating projections of illustrative embodiment 1, include at least a first group of oscillating projections aligned along a first axis of the lamella.

In illustrative embodiment 3, the two or more actuators of the lamellae drive system of illustrative embodiment 1 or 2, include a first actuator configured to drive the lamella in a first direction by applying force to a first sloped surface of the first group of oscillating projections at a first time; and a second actuator configured to drive the lamella in the first direction by applying force to a second sloped surface of the first group of oscillating projections at a second time.

In illustrative embodiment 4, the one or more groups of oscillating projections included in the lamellae drive system as in any of illustrative embodiments 1-3, include a plurality of groups of oscillating projections aligned in an out of phase relationship along separate parallel axes.

In illustrative embodiment 5, the two or more actuators included in the lamellae drive system of any of illustrative embodiments 1-4, include: a first actuator configured to position the lamella within a threshold distance of a target position; and a second actuator configured to provide fine adjustments to a position of the lamella within the threshold distance of the target position.

In illustrative embodiment 6, at least one of the one or more groups of oscillating projections included in the lamellae drive system as in any of illustrative embodiments 1-5 is integral to the lamella.

In illustrative embodiment 7, at least one of the one or more groups of oscillating projections included in the lamellae drive system as in any of illustrative embodiments 1-6 is affixed to the lamella.

In illustrative embodiment 8, the lamellae drive system, as in any of illustrative embodiments 1-7, also includes: a controller including memory storing a program of instructions, and a processor coupled to the memory, the processor configured to execute the program of instructions to cause the controller to control the lamellae drive system to drive a lamella in a direction of motion by extending two or more actuators out of phase with each other, the two or more actuators configured to apply force to one or more sloped surfaces of one or more groups of oscillating projections extending along at least a portion of a length of the lamella parallel to the direction of motion, and determine a current position of the lamella based, at least in part, on positions of the two or more actuators in relation to the one or more groups of oscillating projections.

In illustrative embodiment 9, the processor included in the lamellae drive system of illustrative embodiment 8 is further configured to execute the program of instructions to cause the controller to determine a current position of the lamella based on a number of extension cycles of the two or more actuators and a current extension of the two or more actuators.

In illustrative embodiment 10, the processor included in the lamellae drive system of illustrative embodiment 8 or 9, is further configured to execute the program of instructions to cause the controller to determine the current extension of the two or more actuators based on a voltage applied to the two or more actuators.

In illustrative embodiment 11, the processor included in the lamellae drive system of any of illustrative embodiments 8-10 is further configured to execute the program of instructions to cause the controller to control a direction of movement of the lamella by extending the two or more actuators during times the two or more actuators are located over selected sloped surfaces having heights that increase in the direction of movement of the lamella.

In illustrative embodiment 12, the processor of any of illustrative embodiments 8-11, is further configured to execute the program of instructions to cause the controller to: control a first motive device to position the lamella within a threshold distance of a target position; and control the two or more actuators to provide fine adjustments to the position of the lamella within the threshold distance of the target position.

Illustrative embodiment 13 includes a method comprising: driving a lamella in a direction of motion by extending two or more actuators out of phase with each other, the two or more actuators configured to apply force to particular sloped surfaces of one or more groups of oscillating projections extending along at least a portion of a length of the lamella, a direction of oscillation of the oscillating projections being parallel to a direction of motion of the lamella; and determining a current position of the lamella based, at least in part, on positions of the two or more actuators in relation to the one or more groups of oscillating projection, and/or based on a number of extension cycles of the two or more actuators and a current extension of the two or more actuators.

In illustrative embodiment 14, the method of illustrative embodiment 13, further comprises: controlling a direction of movement of the lamella by extending the two or more actuators during times the two or more actuators are located over selected sloped surfaces having heights that increase in the direction of movement of the lamella.

In illustrative embodiment 15, the method of illustrative embodiment 13 or 14, further comprise: controlling a first a first motive device to position the lamella within a threshold distance of a target position; and controlling the two or more actuators to provide fine adjustments to the position of the lamella within the threshold distance of the target position.

As discussed herein, the terminology "one or more" and "at least one" may be used interchangeably. Furthermore, although the terms first, second, etc. may be used herein to describe various elements, these elements should not be limited by these terms. These terms are only used to distinguish one element from another. For example, a first element could be termed a second element, and similarly, a second element could be termed a first element, without departing from the scope of this disclosure. As used herein, the term "and/or," includes any and all combinations of one or more of the associated listed items.

When an element is referred to as being "connected," or "coupled," to another element, it may be directly connected or coupled to the other element, or more intervening elements may be present. By contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Specific details are provided in the preceding description to provide a thorough understanding of example embodiments. However, it will be understood by one of ordinary skill in the art that example embodiments may be practiced without these specific details. For example, systems may be shown in block diagrams so as not to obscure the example embodiments in unnecessary detail. In other instances, well-known processes, structures, and techniques may be shown without unnecessary detail in order to avoid obscuring example embodiments.

As discussed herein, illustrative embodiments have been described with reference to acts and symbolic representations of operations (e.g., in the form of flow charts, flow diagrams, data flow diagrams, structure diagrams, block diagrams, etc.) that may be implemented as program modules or functional processes include routines, programs, objects, components, data structures, etc., that perform particular tasks or implement particular abstract data types and may be implemented using existing hardware at, for example, existing user equipment or other network elements and/or hardware. Such existing hardware may be processing or control circuitry such as, but not limited to, one or more processors, one or more Central Processing Units (CPUs), one or more controllers, one or more arithmetic logic units (ALUs), one or more digital signal processors (DSPs), one or more microcomputers, one or more field programmable gate arrays (FPGAs), one or more System-on-Chips (SoCs), one or more programmable logic units (PLUs), one or more microprocessors, one or more Application Specific Integrated Circuits (ASICs), or any other device or devices capable of responding to and executing instructions in a defined manner.

Although a flow chart may describe the operations as a sequential process, many of the operations may be performed in parallel, concurrently, or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium," "computer readable storage medium" or "non-transitory computer readable storage medium" may represent one or more devices for storing data, including read only memory (ROM), random access memory (RAM), magnetic RAM, core memory, magnetic disk storage mediums, optical storage mediums, flash memory devices and/or other tangible machine-readable mediums for storing information. The term "computer-readable medium" may include, but is not limited to, portable or fixed storage devices, optical storage devices, and various other mediums capable of storing and/or containing, instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors will perform the necessary tasks. For example, as mentioned above, according to one or more example embodiments, at least one memory may include or store computer program code, and the at least one memory and the computer program code may be configured to, with at least one processor, cause a network element or network device to perform the necessary tasks. Additionally, the processor, memory, and example algorithms, encoded as computer program code, serve as means for providing or causing performance of operations discussed herein.

A code segment of computer program code may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable technique including memory sharing, message passing, token passing, network transmission, etc.

The terms "including" and/or "having," as used herein, are defined as comprising (i.e., open language). The term "coupled," as used herein, is defined as connected, although not necessarily directly, and not necessarily mechanically. Terminology derived from the word "indicating" (e.g., "indicates" and "indication") is intended to encompass all the various techniques available for communicating or referencing the object/information being indicated. Some, but not all, examples of techniques available for communicating or referencing the object/information being indicated include the conveyance of the object/information being indicated, the conveyance of an identifier of the object/information being indicated, the conveyance of information used to generate the object/information being indicated, the conveyance of some part or portion of the object/information being indicated, the conveyance of some derivation of the object/information being indicated, and the conveyance of some symbol representing the object/information being indicated.

According to example embodiments, user equipment, other network elements, or the like, may be (or include) hardware, firmware, hardware executing software or any combination thereof. Such hardware may include processing or control circuitry such as, but not limited to, one or more processors, one or more CPUs, one or more controllers, one or more ALUs, one or more DSPs, one or more microcomputers, one or more FPGAs, one or more SoCs, one or more PLUs, one or more microprocessors, one or more ASICs, or any other device or devices capable of responding to and executing instructions in a defined manner.

Benefits, other advantages, and solutions to problems have been described above with regard to specific embodiments of the invention. However, the benefits, advantages, solutions to problems, and any element(s) that may cause or result in such benefits, advantages, or solutions, or cause such benefits, advantages, or solutions to become more pronounced are not to be construed as a critical, required, or essential feature or element of any or all the claims.

What is claimed is:

1. A lamellae drive system comprising:

a lamella moveably coupled to a carrier, the lamella including a length extending parallel to a direction of motion of the lamella;

one or more groups of oscillating projections along at least a portion of the length of the lamella, a direction of oscillation of the oscillating projections being parallel to the direction of motion of the lamella, and the oscillating projections including opposing sloped surfaces oriented perpendicular to the direction of oscillation; and two or more actuators, each of the two or more actuators having an extendable dimension and being configured to drive the lamella by applying force to particular sloped surfaces of the one or more oscillating projections, the force of the two or more actuators being applied out of phase with each other.

2. The lamellae drive system as in claim 1, wherein the one or more groups of oscillating projections include:

at least a first group of oscillating projections aligned along a first axis of the lamella.

3. The lamellae drive system as in claim 2, wherein the two or more actuators include:

a first actuator configured to drive the lamella in a first direction by applying force to a first sloped surface of the first group of oscillating projections at a first time; and a second actuator configured to drive the lamella in the first direction by applying force to a second sloped surface of the first group of oscillating projections at a second time.

4. The lamellae drive system as in claim 1, wherein the one or more groups of oscillating projections include:

a plurality of groups of oscillating projections aligned in an out of phase relationship along separate parallel axes.

5. The lamellae drive system as in claim 1, wherein the two or more actuators include:

a first actuator configured to position the lamella within a threshold distance of a target position; and a second actuator configured to provide fine adjustments to a position of the lamella within the threshold distance of the target position.

6. The lamellae drive system as in claim 1, wherein at least one of the one or more groups of oscillating projections is integral to the lamella.

7. The lamellae drive system as in claim 1, wherein at least one of the one or more groups of oscillating projections is affixed to the lamella.

8. The lamellae drive system as in claim 1, further comprising:

processing circuitry configured to determine a position of the lamella based on a number of extension cycles associated with the two or more actuators and a current extension amount of the two or more actuators.

9. The lamellae drive system as in claim 8, wherein the processing circuitry is further configured to:

control a direction of movement of the lamella by extending the two or more actuators during times the two or more actuators are located over particular sloped surfaces having heights that increase in a selected direction of movement.

10. The lamellae drive system as in claim 8, wherein at least one of the two or more actuators includes a piezo stack, and the processing circuitry is configured to determine a current extension amount of the piezo stack based on a control voltage applied to the piezo stack.

11. A controller for a lamellae drive system, the controller comprising:

memory storing a program of instructions; and a processor coupled to the memory, the processor configured to execute the program of instructions to cause the controller to control the lamellae drive system to drive a lamella in a direction of motion by extending two or more actuators out of phase with each other, the two or more actuators configured to apply force to one or more sloped surfaces of one or more groups of oscillating projections extending along at least a portion of a length of the lamella parallel to the direction of motion, and determine a current position of the lamella based, at least in part, on positions of the two or more actuators in relation to the one or more groups of oscillating projections.

12. The controller as in claim 11, wherein the processor is further configured to execute the program of instructions to cause the controller to:

determine a current position of the lamella based on a number of extension cycles of the two or more actuators and a current extension of the two or more actuators.

13. The controller as in claim 12, wherein the processor is further configured to execute the program of instructions to cause the controller to:

determine the current extension of the two or more actuators based on a voltage applied to the two or more actuators.

14. The controller as in claim 11, wherein the processor is further configured to execute the program of instructions to cause the controller to:

control a direction of movement of the lamella by extending the two or more actuators during times the two or more actuators are located over selected sloped surfaces having heights that increase in the direction of movement of the lamella.

15. The controller as in claim 14, wherein the processor is further configured to execute the program of instructions to cause the controller to:

control a first actuator to drive the lamella in a first direction by applying force to a first sloped surface of a first group of oscillating projections at a first time; and control a second actuator to drive the lamella in the first direction by applying force to a second sloped surface of a second group of oscillating projections at a second time.

16. The controller as in claim 11, wherein the processor is further configured to execute the program of instructions to cause the controller to:

control a first motive device to position the lamella within a threshold distance of a target position; and control the two or more actuators to provide fine adjustments to the position of the lamella within the threshold distance of the target position.

17. A method comprising:

driving a lamella in a direction of motion by extending two or more actuators out of phase with each other, the two or more actuators configured to apply force to particular sloped surfaces of one or more groups of oscillating projections extending along at least a portion of a length of the lamella, a direction of oscillation of the oscillating projections being parallel to a direction of motion of the lamella; and determining a current position of the lamella based, at least in part, on positions of the two or more actuators in relation to the one or more groups of oscillating projections.

18. The method as in claim 17, further comprising:

determining a current position of the lamella based on a number of extension cycles of the two or more actuators and a current extension of the two or more actuators.

19. The method of claim 17, further comprising:

controlling a direction of movement of the lamella by extending the two or more actuators during times the two or more actuators are located over selected sloped surfaces having heights that increase in the direction of movement of the lamella.

20. The method as in claim 17, further comprising:

controlling a first a first motive device to position the lamella within a threshold distance of a target position; and controlling the two or more actuators to provide fine adjustments to the position of the lamella within the threshold distance of the target position.

* * * * *